United States Patent [19]

Reno et al.

[11] Patent Number: 5,506,342
[45] Date of Patent: Apr. 9, 1996

[54] STABILIZED ANTIBODY FRAGMENTS

[75] Inventors: John M. Reno, Brier; Becky J. Bottino, Lynnwood, both of Wash.

[73] Assignee: NeoRx Corporation, Seattle, Wash.

[21] Appl. No.: 294,792

[22] Filed: Aug. 24, 1994

Related U.S. Application Data

[63] Continuation of Ser. No. 990,165, Dec. 14, 1992, which is a continuation of Ser. No. 647,779, Jan. 30, 1991, abandoned.

[51] Int. Cl.$^6$ ............ A61K 35/16; A61K 39/00; C07K 16/00
[52] U.S. Cl. .................... 530/387.1; 530/387.2; 530/391.1; 530/391.3; 530/391.5; 530/402; 530/404
[58] Field of Search ............ 530/387.1, 387.2, 530/391.1, 391.3, 391.5, 402, 404

[56] References Cited

U.S. PATENT DOCUMENTS

| | | | |
|---|---|---|---|
| 4,470,925 | 9/1984 | Auditore-Hargraves | 424/85 |
| 4,867,973 | 2/1989 | Groens et al. | 424/85.91 |
| 5,055,561 | 10/1991 | Packard et al. | 530/390 |

OTHER PUBLICATIONS

Goldberg et al. Bioconjugate Chem 2:275–280 (1991).
Lamk M. Lamki et al., "Metastatic Colorectal Cancer: Radioimmunoscintigraphy with a Stabilized In–111–labeled F(ab')$_2$ Fragment of an Anti–CEA Monoclonal Antibody[1]", Jan. 1990, vol. 174, pp. 147–151.
Ewa Wasylewska et al., "Stabilization of Human Prostate Acid Phosphatase By Cross–Linking With Diimidoesters", Feb. 1987, vol. 34, pp. 145–156.
D. Scott Wilbur et al., "Development of a Stable Radioiodinating Reagent to Label Monoclonal Antibodies for Radiotherapy of Cancer", Feb. 1989, vol. 30, pp. 216–226.
Glennie et al J. Immunology 139:2367–2375 1987.

*Primary Examiner*—Donald E. Adams
*Attorney, Agent, or Firm*—Burns, Doane, Swecker & Mathis

[57] ABSTRACT

Methods for preparing metabolically stable, covalently crosslinked F(ab')$_2$ fragments of antibody molecules for use in labeled form as in vivo diagnostic and therapeutic agents, the stabilized F(ab')$_2$ fragments so produced in free form or conjugated to a chemical moiety, kits containing such fragments, and methods of using these fragments for diagnosis or therapy, are disclosed. In the method, crosslinking is carried out after reduction of inter-heavy chain disulfide bonds, but before cleavage of the crosslinked antibody to produce the F(ab')$_2$ molecules.

3 Claims, 3 Drawing Sheets

Whole IgG
│
│   a) 50mM DTT
│      25°C
│      15 min.
│   b) desalting column
▼
Reduced IgG
│
│   PDMM, 10 eq.
│      18 hr, R.T.
│      ph=7.5
▼
XL-IgG
│
│   Pepsin
│   pH=4.4
│   18 hr., 37°
▼
XL-F(ab')$_2$
│
│   a) 100mM DTT
│      15 min., 37°
▼   b) purification XL-F(ab')$_2$      (Yield = 70%)

XL = cross-linked
DTT = dithiothreitol
PDMM = p-phenylene dimaleimide

FIG. 2

STABILIZED ANTIBODY FRAGMENTS

CROSS REFERENCE TO RELATED APPLICATIONS

This application is a continuation of application Ser. No. 07/990,165, filed Dec. 14, 1992, which is a continuation application of U.S. patent application No. 07/647,779, filed Jan. 30, 1991, (now abandoned).

FIELD OF THE INVENTION

This invention relates to stabilized, divalent antigen-binding antibody fragments (i.e., F(ab')$_2$ molecules) which may be conjugated to other chemical moieties, such as radionuclides, drugs, or toxins, for use in diagnostic or therapeutic procedures, and methods for making the same.

BACKGROUND OF THE INVENTION

In the past, immunological binding partners such as antibodies and fragments thereof have been used to specifically target molecular sites in vivo. When these immunological binding partners are attached to other chemical moieties, such as radionuclides, such chemical moieties can be delivered specifically to the target sites. Some degree of success has been achieved in specifically localizing radioactivity to tumor markers in vivo utilizing radiolabeled immunological binding partners. Specifically localized radioactivity has been used in vivo for both diagnostic purposes and therapy. For example, radiolabeled immunological binding partners have been used to diagnose deep venous thrombi, to study lymph node pathology, and to detect, stage, and treat neoplasms. Although polyclonal antibodies have previously shown promise for localizing to neoplasms, the development of monoclonal antibodies has provided even greater selectivity of binding and thus more specific targeting of the antibody in vivo.

One of the problems that has accompanied the use of immunological binding partners for diagnosis and therapy has been nonspecific, nontargeted delivery to undesirable sites, even with monoclonal antibodies. For example, administration of radiolabeled antibodies in vivo can result in an undesirable level of background radiation to nontargeted sites such as the liver. Significant background activity can remain for several days after injection even though radiolabeled intact antibody is cleared relatively rapidly from the bloodstream. One approach to reducing the nonspecific delivery of antibodies in vivo has been to fragment the antibodies and to utilize only the portion of the antibodies that specifically binds to an antigen.

To facilitate further discussion of antibody fragments, the following is a brief review of the structure of antibodies. In general, it is well known that antibodies are bifunctional molecules made up of four chains of amino acids and a variety of domains. A simplified model for an IgG antibody molecule showing the basic four-chain structure and domains is shown in FIG. 1. V indicates the variable regions, C the constant regions, and the vertical arrow indicates the so-called hinge region. Thick lines represent heavy (H) and light (L) chains. The thin lines between chains represent disulfide bonds. Cleavage by the enzymes papain and pepsin, which cleave at points indicated in FIG. 1, separates the so-called crystallizable fragment (Fc) from the antigen binding fragment (Fab) region of the antibody. More particularly, cleavage by papain results in two monovalent Fab fragments, whereas cleavage by pepsin produces a single divalent F(ab')$_2$ fragment held together by one or more disulfide bonds between the heavy chains.

It has been previously recognized that the use of Fab and F(ab')$_2$ fragments in radiolabeled form for therapy or diagnosis in vivo can result in reduced radioactive background in vivo, at least in part due to faster clearance rates of these fragments from serum as compared to the intact antibody. Moreover, Fc mediated liver uptake and macrophage binding are also eliminated by use of the Fab or F(ab')$_2$ fragments. Other advantages of the use of these antibody fragments as compared to intact antibody are the following: more rapid tissue distribution, reduced immunogenicity, and enhanced permeability across membranes.

Of the two types of fragments, Fab and F(ab')$_2$, the latter have been determined to have an ideal serum half-life. In general, if the serum half-life is too long, greater amounts of nonspecific targeting will occur. On the other hand, if the serum half-life is too short, not enough specific localization will occur. The serum half-life of murine F(ab')$_2$ fragments in a human is intermediate (about 7 to 8 hours) between intact antibody (24 hours or more) and Fab fragments (1 to 2 hours) and hence, is an advantageous median value. This advantage of the use of F(ab')$_2$ fragments has led to the prediction that these fragments will assume an increasingly important role in immunodiagnostic and therapeutic systems in vivo. See *The Journal of Nuclear Medicine*, 24(4):316–325 (1983).

Examples of studies in which F(ab')$_2$ fragments have been utilized, in radiolabeled form, are the following: *The Journal of Nuclear Medicine*, 27:685–693(1986); *The Journal of Clinical Investigation*, 77:301–311 (1986); and *Cancer Research*, 45:3378–3387 (1985).

In spite of the advantages described above for F(ab')$_2$ antibody fragments in the context of specific delivery of diagnostic and therapeutic agents such as radionuclides to target sites in vivo, some technical problems have arisen in producing such fragments. For example, the present inventors have attempted to make F(ab')$_2$ fragments from an IgG2b antibody referred to as NR-ML-05. Upon cleavage of the intact antibody with pepsin, no useful F(ab')$_2$ fragments are produced; rather, monovalent fragments were produced. See *Handbook of Experimental Immunology, Vol.* 1:*Immunochemistry*, Weir, 4th ed., Blackwell Scientific Pub. (1986). Apparently, the F(ab')$_2$ fragments are not stable to the cleavage conditions. For other antibodies, although the F(ab')$_2$ fragments may be made, attempts to attach them to other chemical moieties has resulted in reduction of specific binding by the antibody or cleavage to the corresponding Fab' fragment.

Accordingly, in spite of the previous advances in this field, there has remained a need for methods of producing stabilized antibody fragments, especially F(ab')$_2$ fragments, so that they may be used more widely.

SUMMARY OF THE INVENTION

The present inventors have discovered ways of stabilizing F(ab')$_2$ molecules. Initially, they attempted to produce stabilized F(ab')$_2$ fragments by crosslinking pairs of monovalent Fab fragments. However, the crosslinking reaction between these monovalent species resulted in polymeric mixtures. Then, the inventors discovered that they could produce stabilized F(ab')$_2$ fragments by first reducing an intact antibody with a reducing agent to break apart the inter-heavy chain disulfide bonds, then covalently crosslinking the exposed sulfhydryl groups, followed by cleaving the crosslinked antibody with a cleaving agent such as pepsin. This discovery is an important aspect of the present invention.

In accordance with the above description, the present invention is directed to methods of forming stabilized F(ab')$_2$ fragments comprising the steps of reducing an antibody molecule, such as an IgG molecule, with a disulfide reducing agent to produce a reduced antibody molecule heaving at least two sulfhydryl groups derived from an inter-heavy chain disulfide bond; reacting the reduced antibody molecule with a bifunctional crosslinking agent that crosslinks the sulfhydryl groups derived from the inter-heavy chain disulfide bond, and then treating the crosslinked antibody molecule with a cleaving agent capable of producing an F(ab')$_2$ molecule from an intact antibody molecule. This process results in stabilized F(ab')$_2$ molecules, which also form part of the present invention.

Such stabilized F(ab')$_2$ molecules may then be used in a variety of reactions, including those that are too harsh for unstabilized F(ab')$_2$ molecules. For example, radiolabeling reactions may be carried out on the stabilized F(ab')$_2$ molecules of this invention. Other diagnostic and therapeutic agents (e.g., drugs, toxins, etc.) may be attached to the stabilized F(ab')$_2$ molecules. Thus, the present invention also has within its scope stabilized F(ab')$_2$ molecules attached (conjugated) to other chemical moieties, kits containing the free or conjugated F(ab')$_2$ molecules, and methods of using these materials for therapy or diagnosis.

BRIEF DESCRIPTION OF THE DRAWINGS

FIG. 2 shows a schematic overview of a specific embodiment of the method of the present invention.

DETAILED DESCRIPTION OF THE PREFERRED EMBODIMENTS

Figure 1:
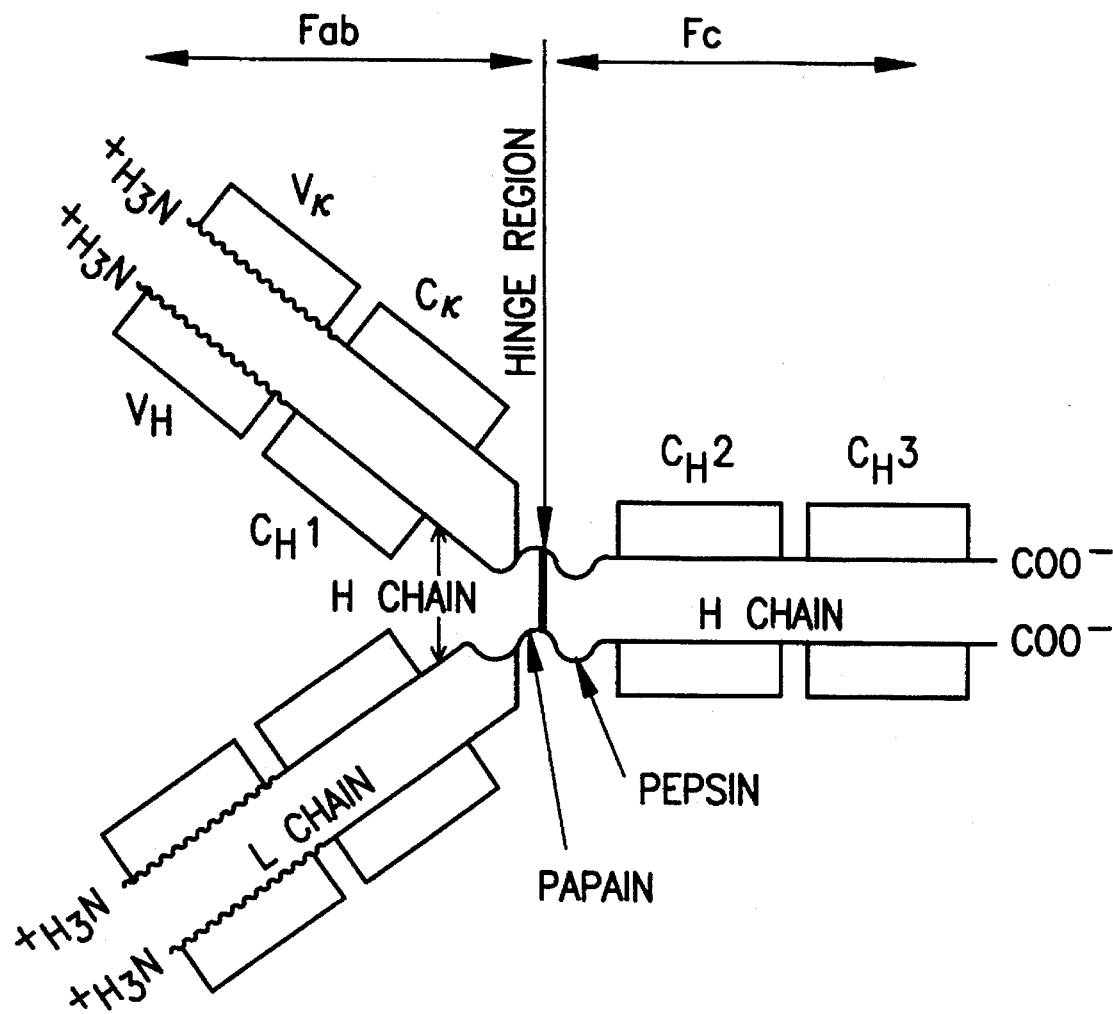
FIG. 1 depicts a simplified model of an IgG 1(κ) human antibody molecule.

Typically, the method of the present invention employs an intact antibody molecule as the starting material. The antibody molecule is preferably either an IgG molecule or an IgM molecule, with the IgG molecules being preferred. Generally, two gamma (γ) heavy chains combined with either two kappa (κ) or two lambda (λ) light chains constitute an IgG molecule, the major class of immunoglobulins in serum. Similarly, two μ heavy chains and two light chains form an IgM subunit; IgM molecules are macroglobulins which consist of five of these basic four-chain subunits. There are four subclasses of gamma chains in humans, γ1, γ2, γ3 and γ4, which yield IgG1, IgG$_2$, IgG3, and IgG4 subclasses of immunoglobulin G molecules, respectively. Any of these different forms of IgG or IgM molecules may be utilized in connection with the present invention.

The intact antibody molecules may be obtained from any species for the purposes of the present invention. For example, human, ape, monkey, mouse, rat, guinea pig, rabbit, dog, cow, horse, fowl, reptile, and amphibian IgG or IgM antibodies could be utilized. The preferred IgG or IgM molecules are those obtained from humans or mice. An especially preferred starting antibody is a γ$_2$B murine antibody. Alternatively, chimeric antibodies (e.g., human-mouse chimeric monoclonal antibodies) may be employed. Recombinant antibodies could also be used. The antibodies may further be polyclonal or monoclonal, the latter being preferred. Although bispecific antibodies are possible starting materials, monospecific antibodies are preferred. By "monospecific" is meant that each of the two Fab ends of the antibody have the same specificity.

As mentioned above, one type of IgG molecule that has been used in the method of the present invention is NR-ML-05, which is a murine monoclonal antibody to a 250 kilodalton antigen associated with human melanoma. F(ab')$_2$ fragments of NR-ML-05 have previously been inaccessible by standard methods. In particular, treatment of NR-ML-05 with pepsin directly (without crosslinking as described herein) results in a monovalent, or Fab fragment.

The first step of the present method involves reducing one or more inter-heavy chain disulfide bonds in the starting antibody. Typically, the reduction will be carried out by treatment of the antibody with a stoichiometric excess of a disulfide reducing agent such as dithiothreitol (DTT) in an aqueous medium, generally of about pH 5–8, preferably pH 6–7. The reaction is allowed to proceed for a sufficient time for substantially all of the antibodies to react with the reducing agent. Usually, the time will be from about 15 minutes to about 6 hours, at temperatures ranging from about 0° to 50° C., usually not exceeding about 40° C., and preferably about 25° C. The particular conditions will be selected in accordance with the particular antibody, the pH, and the like.

Although DTT is the preferred reagent for treatment of the antibody materials, other reducing agents, which may contain a sulfhydryl group or a pair of sulfhydryl groups, may be used, for example: sodium borohydride, sodium phosphorothioate, dithioerythritol (DTE), 2-mercaptoethanol, cysteine, N-acetylcysteine, and glutathione.

Reduction of interchain disulfide bonds does not normally allow dissociation of the antibody chains. Preferably a single inter-heavy chain disulfide will be reduced, but two or more could also be reduced, thereby exposing more than two sulfhydryl groups for crosslinking. It is also possible that intra-heavy-light, inter-light and inter-heavy sulfhydryl groups may be exposed during this reduction step; ordinarily, this does not present any significant problems.

After reduction of the disulfide(s) of the antibody, the reducing agent will normally be removed to avoid interaction in subsequent steps and to avoid any adverse physiological effects. Removal of unreacted and spent reducing agent may be conveniently and efficiently achieved using various chromatographic methods, e.g., cross-linked dextran gel-SEPHADEX™ gel treatment, micropore filtration, etc. The particular manner of separation is not critical to the present invention, as long as significant reoxidation of the sulfhydryls does not occur.

The next step of the present invention is crosslinking of the inter-heavy chain sulfhydryl groups exposed in the reduction step. The type of crosslinking agent is important, particularly with respect to its length at the molecular level. The crosslinking agents that are useful for the present purposes are those that are long enough to result in significant amounts of crosslinking between the heavy chains of a single antibody, but not so long as to result in substantial amounts of crosslinking of sulfhydryls on the heavy chains of two separate antibody molecules. The appropriate length will preferably range from about 10 to about 14 Å between the two crosslinking sites in the crosslinking molecule.

In general, the crosslinking reagent is a bifunctional reagent, i.e., one having two reactive sites, in which both reactive sites are capable of reacting with a sulfhydryl moiety. The crosslinking agent may be homobifunctional or heterobifunctional, i.e., the sites that are reactive with the sulfhydryl moieties may be identical or different, respectively. A preferred homobifunctional crosslinking agent is para-phenylene-dimaleimide (PDMM). Other useful crosslinking agents are bis-maleimido-n-hexane; bis-maleimido-cyclohexane, dimaleimido methyl ether, and compounds having active iodo moieties as the reactive centers.

The crosslinking step will usually be carried out with an excess of the crosslinking agent, typically about 2 to 12 equivalents of agent relative to the antibody. The remaining conditions can readily be ascertained based on conventional techniques in the art. The specific conditions for crosslinking are not critical for the purposes of the present invention; however, it is important that the crosslinking take place prior to generation of F(ab')$_2$ fragments.

The next step in the present method involves generation of F(ab')$_2$ fragments from the crosslinked antibody molecule. As used herein "F(ab')$_2$ fragments" are divalent antigen-binding portions of antibodies separated from the crystallizable portion (Fc). They are usually produced from an intact antibody by enzymatic cleavage on the carboxy terminus side of the hinge region of the heavy chains. The cleavage step herein may be carried out in a manner that is analogous to steps used to generate F(ab')$_2$ fragments from intact antibody that has not been crosslinked. A preferred cleaving agent is pepsin, which is used at an acid pH, preferably pH 4–5. The time period and temperature can be determined based on the known properties of pepsin.

It is also possible to use other cleaving agents, such as papain, S. aureus V8, or lysine endoprotease.

The above-described cleavage step is designed to produce a crosslinked F(ab')$_2$ fragment, which is referred to herein as a stabilized F(ab')$_2$ fragment. The stabilized F(ab')$_2$ fragment may be isolated and purified at this stage, e.g., for use subsequently to produce a diagnostic or therapeutic agent, or it may be used directly as a reactant in a subsequent step.

The stabilized F(ab')$_2$ fragments may be attached to any other chemical moiety as desired. The specific nature of the moiety attached to the antibody fragment is not critical. For example, the F(ab')$_2$ fragments may be attached to radioactive moieties (atoms or molecules), toxins, enzymes, chemical reporter groups (e.g., chemiluminescent groups, spin labeled groups, chromophores and drugs), etc. Procedures for attaching such diagnostic and therapeutic agents to antibodies (and fragments thereof) are known. The particular mode of attachment is also not critical, although preferably it will be covalent.

Examples of toxins which may be employed are ricin, abrin, diphtheria toxin, Pseudomonas exotoxin A, ribosomal inactivating proteins, and mycotoxins; e.g., trichothecenes. Trichothecenes are a species of mycotoxins produced by soil fungi of the class *Fungi imperfecti* or isolated from *Baccharus megapotamica* (Bamburg, J. R., *Proc. Molec. Subcell. Bio.* 8:41–110, 1983; Jarvis & Mazzola, *Arc. Chem. Res.* 15:338–395, 1982). Therapeutically effective modified toxins or fragments thereof, such as those produced through genetic engineering or protein engineering techniques, may be used.

Any suitable therapeutic drug may be employed, depending on the nature of the illness to be treated. Among the many therapeutic drugs that have been used to treat various forms of cancer are nitrogen mustards such as L-phenylalanine nitrogen mustard and cyclophosphamide, intercalating agents such as cis diamino dichloro platinum, antimetabolites such as 5-fluorouracil, vinca alkaloids such as vincristine, and antibiotics such as bleomycin and anthracycline antibiotics, e.g., doxorubicin, daunorubicin, and derivatives thereof.

A preferred derivative of a stabilized F(ab')$_2$ fragment for purposes of the present invention is one that is radiolabeled with a radionuclide.

Radionuclide metal chelates are one type of radiolabeled molecule that may be employed. Many chelating compounds of various structures, as well as methods for the synthesis and radiolabeling thereof to produce radionuclide metal chelates, are known. Chelating compounds comprising various combinations of sulfur, nitrogen, oxygen, and phosphorus donor atoms may be used, for example. In one embodiment of the invention, the chelating compound comprises a total of from four to six donor atoms selected from nitrogen and sulfur atoms. During the radiolabeling procedure, bonds form between the donor atoms and the radionuclide metal, thereby producing a radionuclide metal chelate.

One type of chelating compound that may be employed comprises two nitrogen and two sulfur donor atoms and thus may be designated an "N$_2$S$_2$" chelating compound. Suitable N$_2$S$_2$ chelating compounds are described in U.S. Pat. No. 4,897,255, entitled "Metal Radionuclide Labeled Proteins for Diagnosis and Therapy", which is hereby incorporated by reference in its entirety. Methods for radiolabeling the chelating compounds and attachment of proteins (including antibody fragments) to the compounds are also disclosed in U.S. Pat. No. 4,897,255.

The chelating compound is radiolabeled with a radionuclide metal. Radionuclide metals include, but are not limited to, the diagnostically effective radionuclide $^{99m}$Tc, and the therapeutically effective radionuclides $^{188}$Re, $^{186}$Re, $^{67}$Cu, $^{64}$Cu, $^{212}$Pb, $^{212}$Bi, $^{111}$In, $^{90}$Y, and $^{109}$Pd. $^{99m}$Tc, $^{186}$Re and $^{188}$Re are preferred radionuclide metals for use in the present invention. Procedures for preparing these isotopes are known. Molybdenum/technetium generators for producing $^{99m}$Tc are commercially available. Procedures for producing $^{186}$Re include the procedures described by Deutsch et al., (*Nucl. Med. Biol.* Vol. 13:4:465–477, 1986) and Vanderheyden et al., (*Inorganic Chemistry*, Vol. 24:1666–1673, 1985), and methods for production of $^{188}$Re have been described by Blachot et al. (*Intl. J. of Applied Radiation and Isotopes*, Vol. 20:467–470, 1969) and by Klofutar et al. (*J. of Radioanalytical Chem.*, Vol. 5:3–10, 1970). Production of $^{109}$Pd is described in Fawwaz et al., *J. Nucl. Med.* 25:796, 1984. Production of $^{212}$Pb and $^{212}$Bi is described in Gansow et al., *Amer. Chem. Soc. Syrup. Ser.* 241:215–217, 1984, and Kozah et al., *Proc. Nat'l. Acad. Sci.* USA 83:474–478, 1986.

The radiolabeling reaction (for the N$_2$S$_2$ compound and the other chelating compounds described below) is conducted using conventional procedures. For example, pertechnetate ($^{99m}$TcO$_4^-$) or perrhenate ($^{186}$ or $^{188}$ReO$_4^-$) are generally contacted with a chelating compound in the presence of a reducing agent (e.g., a ferrous or stannous salt or dithionite) to effect reduction of the radionuclide to an oxidation state at which chelation can occur. Alternatively, the pertechnetate or perrhenate may be reduced in the presence of a relatively labile complexing agent such as gluconic acid or citric acid to form intermediate complexes ($^{99m}$Tc-gluconate or $^{188}$Re-citrate). When the intermediate complexes are contacted with the chelating compound under appropriate reaction conditions (which may involve heating), the radionuclide metal is transferred to the chelating compound, thereby producing a stable radionuclide metal chelate.

Chelates of $^{212}$Pb, $^{212}$Bi and $^{109}$Pd may be prepared by combining the appropriate salt of the radionuclide with the chelating compound and incubating the reaction mixture at room temperature or at higher temperatures. It is not necessary to treat the lead, bismuth, palladium, and copper radioisotopes with a reducing agent prior to chelation, as such isotopes are already in an oxidation state suitable for chelation. The specific radiolabeling reaction conditions may vary somewhat according to the particular radionuclide and chelating compound involved.

Additional $N_2S_2$ chelating compounds comprising carboxylic acid substituent(s) for improved biodistribution properties and the use thereof for radiolabeling proteins such as antibody fragments, are described in copending U.S. patent application Ser. No. 07/367,502, entitled "Radionuclide Metal Chelates for the Radiolabeling of Proteins", which is hereby incorporated by reference in its entirety.

Another type of chelating compound that may be employed comprises one sulfur and three nitrogen donor atoms and thus may be designated an "$N_3S$" chelating compound. Suitable $N_3S$ chelating compounds include those described in U.S. Pat. No. 4,965,392, issued Oct. 23, 1990, entitled "Chelating Compounds for Metal-Radionuclide-Labeled Proteins", which is hereby incorporated by reference in its entirety.

Other chelating compounds may have different combinations of donor atoms. Such compounds include, among others, the $N_2S_4$, $N_2S_3$, and $N_3S_3$ chelating compounds useful for radiolabeling proteins, which are described in copending U.S. patent application Ser. No. 07/201,134, entitled "Metal Radionuclide Chelating Compounds for Improved Chelation Kinetics", which is hereby incorporated by reference in its entirety. In addition, the $N_2S_2$ and $N_3S$ compounds presented above may comprise varying numbers of substituents such as carboxylic acid groups and from 0 to 3 oxygen atoms (=O) attached to carbon atoms of the chelate core.

In one embodiment of the present invention, the chelating compounds comprise, or are attached to, clearable linkers. A number of linkers that are clearable under defined conditions (e.g., at acidic pH, under reducing conditions, or in the presence of an enzyme such as a protease) are known. The chelates therefore may be released from the stabilized F(ab')$_2$ molecule under the desired conditions (e.g., at a desired target site in vivo).

Suitable chelating compounds comprising a clearable linkage include but are not limited to those described in copending U.S. patent application Ser. No. 07/457,480, entitled "Radiolabeled Proteins for Diagnostic and Therapeutic Use", which is hereby incorporated by reference in its entirety. The U.S. Ser. No. 07/457,480 application discloses $N_2S_2$ and $N_3S$ chelating compounds comprising a linker of defined structure that terminates in a chemically reactive functional group. The linkage is cleavable at an ester group positioned in a particular orientation therein.

Other examples of radiolabeled molecules that may be attached to the stabilized F(ab')$_2$ molecule of the present invention include radiohalogenated molecules. Examples of molecules that bind radiohalogens at the meta or para position on a phenyl ring are described in U.S. Pat. No. 4,885,153, entitled "Radiohalogenated Proteins", which is hereby incorporated by reference in its entirety. Suitable radiohalogens include radioisotopes of iodine, bromine, fluorine, and astatine.

Additional radiohalogenated molecules that may be used in the present invention are described in U.S. Pat. No. 4,876,081, entitled "Vinyl Substituted Radiohalogen and Methods of Use of Conjugates", which is hereby incorporated by reference in its entirety.

Antibodies may further be radiolabeled with $^{111}$In by standard procedures, such as the ones exemplified in Meares et al. Anal. Biochem. 142:68–78 (1984).

Another aspect of the present invention involves kits that contain stabilized F(ab')$_2$ fragments or derivatives thereof. These kits may also contain standard reagents and materials for conjugating a chemical group with the stabilized F(ab')$_2$ molecules (if they are not already conjugated), instructions, suitable controls and any other standard kit components known to those of ordinary skill. In one embodiment of the invention, the kit comprises both stabilized F(ab')$_2$ fragments and a chelating compound which may be attached to the stabilized F(ab')$_2$ fragments.

The subject labeled products may be administered to a mammalian host intravenously, intra-arterially, peritoneally, intratumorally, or subcutaneously, depending upon the particular site at which the chemical group is desired. Generally, the amount to be injected into a host will depend upon the size of the host. When the label is a radiolabel, about 1 to 3000 μCi/kg of host will typically be administered. For human hosts, the dosage of radiolabeled F(ab')$_2$ molecules will usually be about 10–50 mCi/70 kg host, more usually about 25–35 mCi/70 kg host; for lower mammals, e.g., mice, the dose will be about 25–100 μCi for biodistribution studies, while up to or greater than 1000 μCi for imaging studies. After administration of the radionuclide, depending upon its purpose, the host may be treated in various ways for detection or therapy.

The invention now being generally described, the same will be better understood by reference to certain specific examples which are included herein for illustrative purposes only, and are not intended to be limiting of the present invention.

EXAMPLE I

A solution of 20 mg of NR-ML-05 intact antibody is concentrated by ultrafiltration to a final concentration of 10 mg/mL in Phosphate Buffered Saline (PBS). Dithiothreitol (DTT) dissolved in water is added to the NR-ML-05 solution to a final concentration of 50 mM. The antibody solution containing the DTT is allowed to stand at room temperature for 15 minutes, during which time reduction of the inter- and intra-chain disulfide bonds occurs. The heavy and light chains the antibody continue to be held together by the tertiary structure of the molecule. Size-exclusion HPLC analysis of the reduced NR-ML-05 antibody using a Zorbax G-250 column shows no change in the antibody profile.

The excess reducing agent is removed from the NR-ML-05 antibody solution using a Pharmacia PD-10 desalting column eluted with PBS. The fractions containing the reduced NR-ML-05 are collected and pooled.

p-Phenylene dimaleimide (PDMM) is dissolved in DMSO at a concentration of 1 mg/mL. Ten equivalents of PDMM are immediately and slowly added to the reduced NR-ML-05 solution while stirring at room temperature. The solution is allowed to stir at 25° C. overnight (approx. 18 hr.).

The crosslinked intact NR-ML-05 (XL•NR-ML-05) is then concentrated to 1 mL (approx. 20 mg/mL) by ultrafiltration (Amicon Stirred Cell with PM-30 membrane). The excess crosslinking agent is removed and buffer exchange is achieved simultaneously by passing the XL•NR-ML-05 solution over a PD-10 column equilibrated and eluted with 20 mM Acetate Buffer, pH 4.4. The fractions containing the XL•NR-ML-05 are collected and pooled.

Soluble pepsin is dissolved in 20 mM Acetate Buffer, pH 4.4, to a concentration of 1 mg/mL. Pepsin is added to the XL•NR-ML-05 solution to a final antibody:enzyme ratio of 1:50. The enzyme antibody solution is stirred at 37° C. for 24 hours. Digestion is monitored during this time by size-exclusion HPLC using a Zorbax G-250 column. At 24 hours XL•NR-ML-05 shows 80% digestion to F(ab')$_2$ fragments. The pH of the solution is raised to 7.5 using 0.2M Phosphate Buffer pH 7.5 to stop the digestion.

DTT is added to the digested XL•NR-ML-05 solution to a final concentration of 100 mM. The solution is allowed to stand for 15 minutes at 37° C. This process reduces any non-crosslinked F(ab')$_2$ species to Fab'.

The antibody solution is purified and buffer exchanged into PBS by ultrafiltration.

Final purification of the XL•NR-ML-05 F(ab')$_2$ is achieved using a preparative TSK-3000 column. The peak corresponding to XL•NR-ML-05 F(ab')$_2$ is collected and concentrated to 1 mg/mL.

The purified XL•NR-ML-05 F(ab')$_2$ is characterized by size exclusion HPLC, ELISA immunoreactivity and SDS-PAGE (reduced and non-reduced). HPLC shows a single peak at a retention time of 9.5 min. (MW~100 Kd) (Intact= 8.9 RT). ELISA immunoreactivity is 85 IR Units (Intact~100 IR). Reduced and non-reduced SDS-PAGE show identical patterns. Treatment of XL•NR-ML-05 F(ab')$_2$ with 200 mM DTT shows no reduction to Fab' by size exclusion HPLC.

EXAMPLE II

The stabilized F(ab')$_2$ antibody fragment produced in Example I is radiolabeled using a chelating compound designated as an "N$_2$S$_2$" chelating compound. The synthesis and use of such chelating compounds is described in U.S. Pat. No. 4,897,255. One example of an N$_2$S$_2$ chelating compound is as follows:

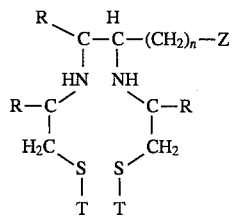

wherein n is from 1 to about 4, preferably 2; each R independently is selected from =O and H$_2$; T represents a sulfur protecting group (preferably a hemithioacetal such as an ethoxyethyl group); and Z represents an active ester or other reactive functional group useful for attaching the chelating compound (before or after radiolabeling) to the stabilized antibody fragment.

The N$_2$S$_2$ chelating compound may be radiolabeled to produce a radionuclide metal chelate of the following formula:

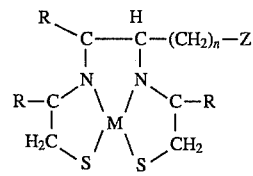

wherein M represents a radionuclide metal or oxide thereof and the other symbols are as described above.

In one embodiment of the present invention, the stabilized F(ab')$_2$ molecule radiolabeled using the following N$_2$S$_2$ chelating compound:

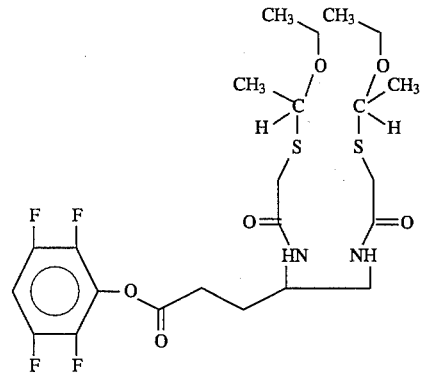

One mL of sodium pertechnetate (about 100 mCi, eluting from a $^{99}$Mo/$^{99}$Tc generator) is added to a vial containing a lyophilized preparation comprising 5 mg sodium gluconate, 0.12 mg stannous chloride dihydrate, about 0.1 mg gentisic acid as a stabilizer, and about 20 mg lactose as a filler to aid lyophilization. After gentle agitation to mix the contents, the vial is incubated at room temperature for 10 minutes to form a $^{99m}$Tc-gluconate complex.

A separate vial containing the chelating compound in dry solid form is prepared by dispensing a solution of 0.3 mg of the chelating compound in acetonitrile into a vial, then removing the solvent under N$_2$ gas. To this vial is then added 0.9 mL of 100% isopropyl alcohol, and the vial is gently shaken for about two minutes to completely dissolve the chelating compound. Next, 0.6 mL of this solution of the chelating agent is transferred to a vial containing 0.16 mL of glacial acetic acid/0.2N HCl (2:14), and the vial is gently agitated. Of this acidified solution, 0.5 mL is transferred to the vial containing the $^{99m}$Tc-gluconate complex prepared above. After gentle agitation to mix, the vial is incubated in a 75°±2° C. water bath for 15 minutes, then immediately transferred to a 0° C. ice bath for two minutes. The $^{99m}$Tc-labeled N$_2$S$_2$ chelate is thus produced.

To a separate vial containing 10 mg of the stabilized F(ab')$_2$ antibody fragment (prepared in Example I) in 0.5 mL of phosphate-buffered saline, is added 0.4 mL of 1.0M sodium bicarbonate buffer, pH 10.0. The vial is gently agitated.

The vial containing the acidified solution of the $^{99m}$Tc-labeled radionuclide metal chelate (produced above) is removed from the ice bath, 0.1 mL of 1.0M sodium bicarbonate buffer, pH 10.0 is added, and the vial is agitated to mix. Immediately, the buffered stabilized F(ab')$_2$ fragment solution is added, the vial is gently agitated to mix, and then incubated at room temperature for 20 minutes to allow attachment of the radionuclide metal chelate to the stabilized antibody fragment. The 2,3,5,6,-tetrafluorophenyl ester of the chelate reacts with amines on lysine residues of the antibody fragment to produce amide bonds. A column containing an anion exchanger, either DEAE-SEPHADEX or QAE-Sephadex, is used to purify the radiolabeled stabilized F(ab')$_2$ molecule.

EXAMPLE III

A pharmacokinetic study in mice was undertaken to allow a comparison of biodistribution of radiolabeled crosslinked and noncrosslinked F(ab')$_2$ fragments. The antibody employed for this study is referred to as 9.2.27.

Figure 3A:
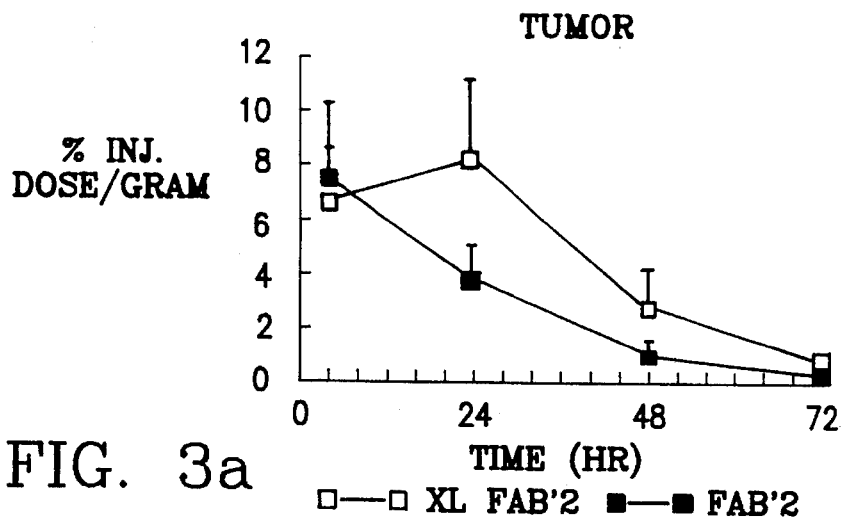
FIGS. 3A–3C shows the results of a pharmacokinetic study comparing radiolabeled F(ab')$_2$ and crosslinked F(ab')$_2$ fragments in mice.
Figure 3B:
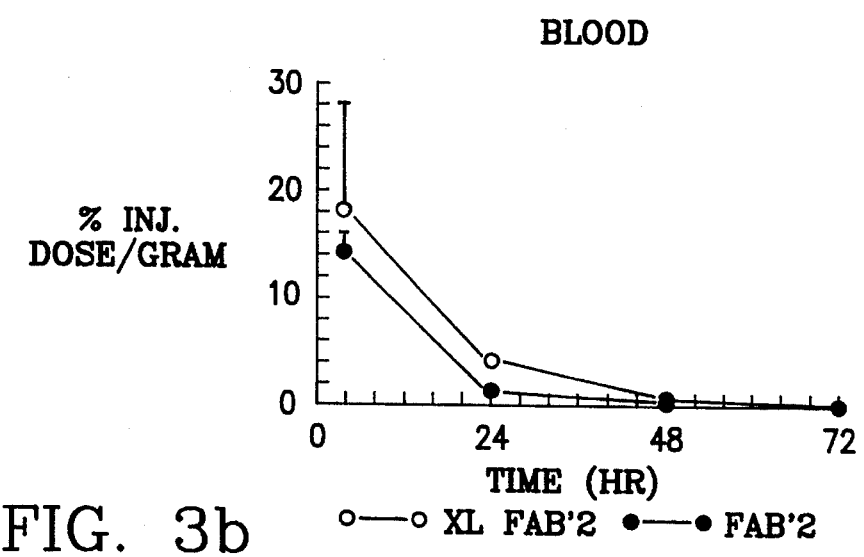
Figure 3C:
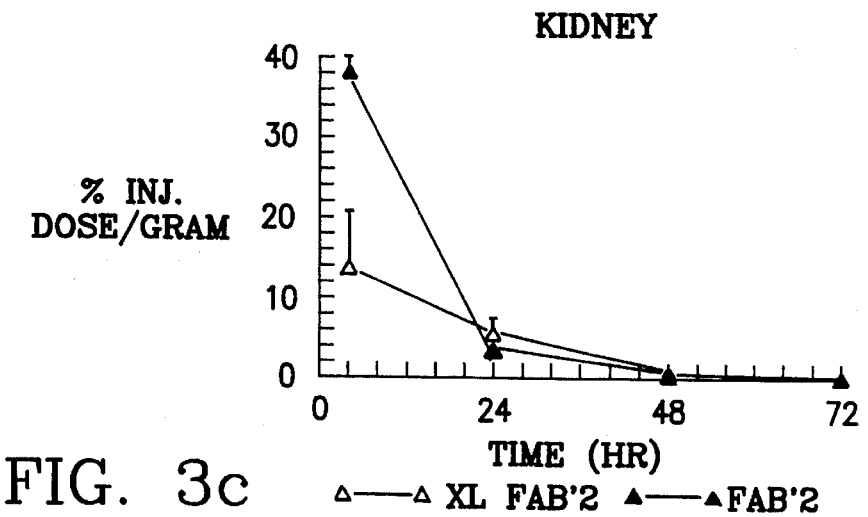

FIG. 3 shows the results of the study comparing 9.2.27 F(ab')$_2$ with crosslinked (XL) 9.2.27 F(ab')$_2$. In this study 9.2.27 F(ab')$_2$ was radiolabeled with $^{125}$I and 9.2.27 XL F(ab')$_2$ was radiolabeled with $^{131}$I using the PIP radiolabeling procedure. See U.S. Pat. No. 4,885,153, entitled "Radiohalogenated Proteins"). Ten micrograms of $^{125}$I F(ab')$_2$ and ten micrograms of $^{131}$I XL F(ab')$_2$ were coinjected into each of 16 nude mice in which Belovsky melanoma xenografts had been previously implanted. Percent injected dose per gram of each radionuclide was determined at 4, 24, 48, and 72 hours for various organs. The crosslinked F(ab')$_2$ demonstrated a prolonged blood half life, extended tumor retention, and lower kidney uptake as compared to the unmodified antibody. These observed changes are consistent with predicted stabilizing effects of a crosslinked F(ab')$_2$ fragment. These changes in biodistribution are of potential therapeutic value in the use of crosslinked fragments to increase tumor dose while decreasing dose to nontarget organs.

The invention now being fully described, it will be apparent to one of ordinary skill in the art that many changes and modifications can be made thereto, without departing from the spirit or scope or the invention as set forth herein.

The embodiments of the invention in which an exclusive property or privilege is claimed are defined as follows:

1. A method of preparing a stabilized monospecific F(ab')$_2$ IgG$_{2b}$ antibody molecule, the method comprising:

reducing an intact IgG$_{2b}$ antibody molecule with a disulfide reducing agent to reduce the inter-chain and intra-chain disulfide bonds;

reacting said reduced inter-chain and intra-chain disulfide bonds with a bifunctional crosslinking agent that cross links said disulfide bonds to form a crosslinked intact IgG$_{2b}$ antibody molecule; and reacting the crosslinked intact IgG$_{2b}$ antibody molecule with a cleaving agent capable of producing a F(ab')$_2$ molecule from said antibody, to thereby produce a stabilized F(ab')$_2$ IgG$_{2b}$ antibody molecule.

2. A method according to claim 1, further comprising labeling said stabilized F(ab')$_2$ molecule with a radionuclide.

3. A method according to claim 2, wherein said radionuclide is selected from the group consisting of $^{99m}$Tc, $^{186}$Re, $^{188}$Re, $^{67}$Cu, $^{111}$In, and $^{90}$Y.

* * * * *